United States Patent
Kwak et al.

(10) Patent No.: US 7,018,820 B2
(45) Date of Patent: Mar. 28, 2006

(54) METHOD OF REMOVING RESIDUAL ENZYMES IN ENZYME MICROENCAPSULATION

(75) Inventors: Hae-Soo Kwak, 101-601, Hyundai Apt., 70-5 Dunchon-dong, Kangdong-ku, Seoul (KR); Joon Bum Lee, Anyang (KR)

(73) Assignee: Hae-Soo Kwak, Seoul (KR)

( * ) Notice: Subject to any disclaimer, the term of this patent is extended or adjusted under 35 U.S.C. 154(b) by 603 days.

(21) Appl. No.: 10/196,202

(22) Filed: Jul. 17, 2002

(65) Prior Publication Data

US 2003/0148483 A1    Aug. 7, 2003

(30) Foreign Application Priority Data

Jan. 28, 2002   (KR) ................. 2002-4843

(51) Int. Cl.
   *C12N 11/04* (2006.01)
   *C12N 11/00* (2006.01)
(52) U.S. Cl. ........................ 435/182; 435/174
(58) Field of Classification Search ................. 435/183
   See application file for complete search history.

(56) References Cited

U.S. PATENT DOCUMENTS

| 6,024,766 | A  | * | 2/2000  | Wasinger ........................ 8/111 |
| 6,767,728 | B1 | * | 7/2004  | Yang et al. ................. 435/207 |
| 6,803,066 | B1 | * | 10/2004 | Traeder et al. .............. 426/333 |

OTHER PUBLICATIONS

Kwak et al., J, Diary. Sci., vol. 84, No. 7, pp. 1576-1582 (2001).

* cited by examiner

*Primary Examiner*—Christopher R. Tate
*Assistant Examiner*—Amanda P. Wood
(74) *Attorney, Agent, or Firm*—Birch, Stewart, Kolasch & Birch, LLP

(57) ABSTRACT

Disclosed is a method of removing residual enzymes when microencapsulating enzymes, and more particularly, for inactivating enzymes remaining in an uncapsulated form during microencapsulation of enzymes by treating dispersion fluid of microcapsules containing enzymes with ozone, together with removal of microorganisms harmful to human beings, where the ozone treatment is conducted for 1–10 min with 1–10 ppm of ozone generated from a UV lamp in a range from 150 to 200 nm wavelength.

4 Claims, 3 Drawing Sheets

METHOD OF REMOVING RESIDUAL ENZYMES IN ENZYME MICROENCAPSULATION

TECHNICAL FIELD

The present invention relates, generally, to a method of removing residual enzymes when microencapsulating enzymes, and more particularly, to a method of inactivating enzymes remaining in an uncapsulated form during microencapsulation of enzymes by treating a dispersion solution of microcapsules containing enzymes with ozone, together with removal of microorganisms harmful to human beings.

BACKGROUND ART

Milk, which is nutritious, is a universal food. However, a large number of people have difficulty in digesting lactose, a major nutrient of milk, owing to lack of lactase, β-galatosidase. To solve this problem, lactase is added to milk during milk processing.

In spite of such an effort, most consumers do not prefer milk containing lactase because hydrolysis of lactose mediated by lactase increases the sweetness of milk to several times higher than normal milk.

In order to solve this problem, there was employed a microencapsultion method by which enzymes are microencapsulated, but uncapsulated enzymes remains in dispersion fluid to hydrolyze lactose, thus they increase sweetness of milk. For this reason, residual enzymes should be eliminated.

It was reported that the residual enzymes can be removed by centrifugation (H. S., Kwak, M. R. Ihm, and J. Ahn., 2001. Microcapsulation of β-galactosidase with fatty acid esters. J. Dairy Sci. 84:1576–1582). However, the centrifugation method has conspicuous disadvantages of being non-economical industrially owing to high cost large-scale centrifuges, and high production cost resulting from requirement of two or three centrifugation steps.

DISCLOSURE OF THE INVENTION

Leading to the present invention, the intensive and thorough research into methods of removing uncapsulted enzymes, conducted by the present inventors with an aim to solve the problems encountered in prior arts, resulted in the finding that, instead of centrifugation, an ozone treatment makes it possible to remove uncapsulated enzymes as well as microorganisms harmful to human beings.

Thus, it is an object of the present invention to provide a new method of removing residual enzymes remaining in an uncapsulated form during microencapsulation of enzymes, as well as microorganisms harmful to human beings.

BRIEF DESCRIPTION OF THE DRAWING

The above and other objects, features and other advantages of the present invention will be more clearly understood from the following detailed description taken in conjunction with the accompanying drawings, in which.

BEST MODES FOR CARRYING OUT THE INVENTION

With the aim of achieving the above object, there is provided a method of removing residual enzymes not trapped in microcapsules upon microencapsulating enzymes, with which the residual enzymes are inactivated through an ozone treatment of dispersion fluid of enzymes.

The ozone molecule ($O_3$), which consists of three oxygen atoms, and has a molecular weight of 48, is very effective in inactivating or killing pathogenic microorganisms, such as bacteria or viruses, thus being utilized for disinfection of water supply and sewer systems and preservation of food, based on permission from the Food and Drug Administration (FDA) recognizing safety of such ozone treatment.

In the present invention, there is used an ozone generator equipped with an ultraviolet (UV) lamp emitting UV light of 150–200 nm that can generate ozone. In accordance with the present invention, dispersion fluid of microcapsules entrapping enzymes is treated with 1–10 ppm of ozone to inactivate residual enzymes. It is preferable that the ozone treatment is performed under a dry oxygen pressure of 0.4–0.6 kg/cm$^2$ and a flow rate of 5–15 L/min.

Microcapsules are typically prepared by spraying a mixture comprising enzymes and a solution of coating material over a surfactant-dissolved solution chilled in advance, to promote the formation of microcapsules, and centrifuging the resulting dispersion fluid of microcapsules to remove untrapped enzymes in addition to intact capsules not containing enzymes from the fluid. However, during this conventional microencapsulation process in which enzymes are sprayed over a dispersion fluid, some enzymes remain in an uncapsulated form in a dispersion fluid even after centrifugation.

Figure 1:
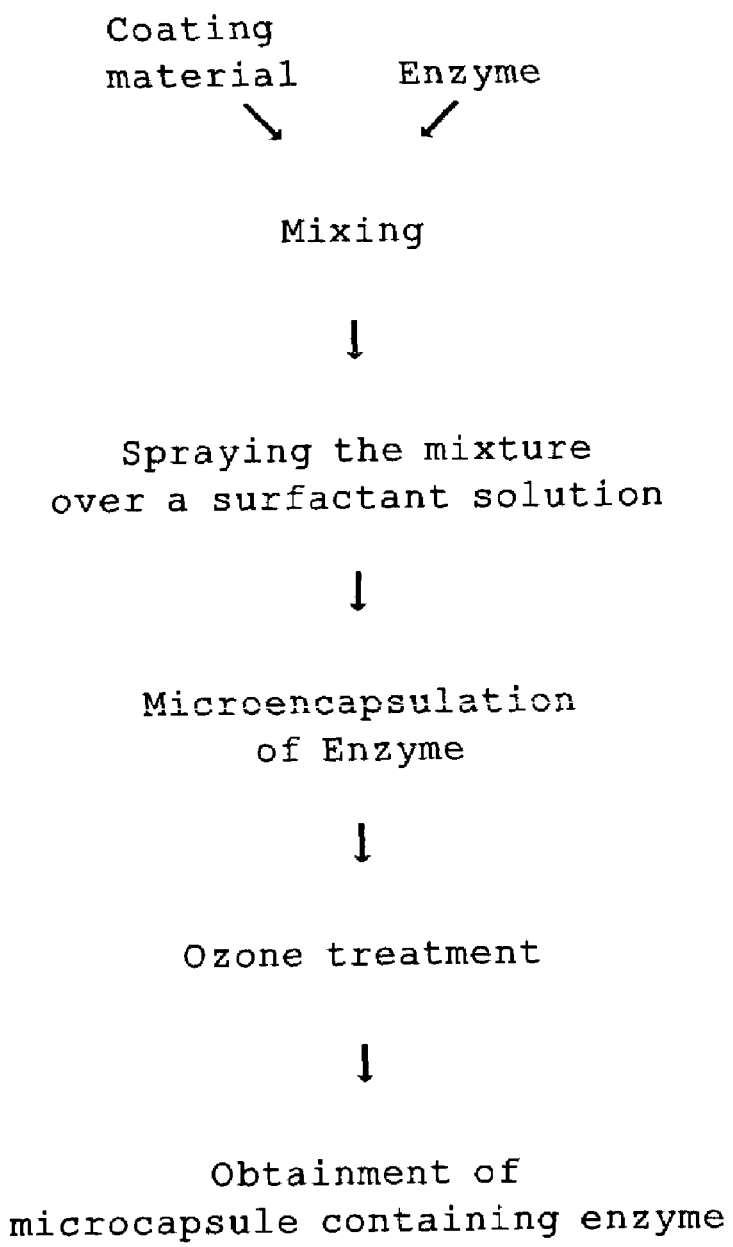
FIG. 1 is a flow chart showing a method of removing residual enzymes when microencapsulating enzymes.

In accordance with the present invention, with reference of FIG. 1, microencapsultion of enzymes is completed through ozone treatment of a dispersion fluid of enzymes prepared according to the same method as above. In an embodiment, lactase are microencapsulated.

In accordance with the present invention, the activity of uncapsulated lactase, which may remain after a microencapsulation process, is evaluated. Effect of ozone treatment on microencapsulated lactase is investigated.

Also, effect of ozone on the growth of pathogenic microorganisms is examined in order to verify the disinfection efficiency of ozone. Sensory property of milk containing ozone-treated microcapsules is evaluated during storage.

Having generally described this invention, a further understanding can be obtained by reference to certain specific examples which are provided herein for purposes of illustration only and are not intended to be limiting unless otherwise specified.

EXAMPLE 1

Preparation of Microcapsules

Lactase was microencapsulated using PGMS (polyglycerol monostearate). Since PGMS is present in a solid state at room temperature and thus difficult to spray, PGMS was dissolved in distilled water in a ratio of 5:4 (w/v), followed by heating at 55° C. for 20 min and then mixing with stirring at 1,200×g for 1 min.

Pre-heated to 55° C. for 2 min to increase the activity of lactase, the PGMS solution was mixed with lactase at a ratio of 15:1, and the mixture was then sprayed over a solution of 0.05% Tween-60 maintained at 5° C., using an airless paint sprayer (W-300 spray gun, Wagner Spray Tech. Co., Markdorf. Germany), resulting in formation of microcapsules.

Lactase used in this example was Vita Netural lactase VNL 5000 (Culture Systems Inc, Mishawake Ind., USA), featured in that specific activity is 504 unit/g. Used as a coating material, PGMS, which is a kind of fatty acid ester, was purchased from I1-Shin Emulsifier Co., Ltd.

EXAMPLE 2

Ozone Treatment

Using an ozone generator (Korea Ozone Tech., AOP type, Korea), 100 ml of the dispersion fluid of microcapsules entrapping lactase prepared in Example 1 was treated with 1 ppm of ozone, which was produced by UV light of 150–200 nm wavelength, with direct bubbling for 1, 5, and 10 min under a dry oxygen pressure of 0.5 kg/cm$^2$ and a flow rate of 10 L/min, where ozone was transmitted through a tube.

EXAMPLE 3

Ozone Treatment

Using an ozone generator (Korea Ozone Tech., AOP type, Korea), 100 ml of the dispersion fluid of microcapsules entrapping lactase prepared in Example 1 was treated with 5 ppm of ozone, which was produced by UV light of 187 nm wavelength, with direct bubbling for 1, 5, and 10 min under a dry oxygen pressure of 0.5 kg/cm$^2$ and a flow rate of 10 L/min, where ozone was transmitted through a tube.

EXAMPLE 4

Ozone Treatment

Using an ozone generator (Korea Ozone Tech., AOP type, Korea), 100 ml of the dispersion fluid of microcapsules entrapping lactase prepared in Example 1 was treated with 10 ppm of ozone, which was produced by UV light of 187 nm, with direct bubbling for 1, 5, and 10 min under a dry oxygen pressure of 0.5 kg/cm$^2$ and a flow rate of 10 L/min, where ozone was transmitted through a tube.

Experimental Example 1

Assay for the Activity of Uncapsulated Lactase

After centrifuging the dispersion fluid of microcapsules prepared by ozone treatment in Examples 2 to 4 at 24,900×g for 10 min, the resulting supernatants were assayed for activity of uncapsulated lactase.

A portion of each of the supernatants was primarily filtered using Whatman No. 540 (Whatman International Ltd., Maidstone, England), and then further filtered using an 1 μm membrane filter (Whatman International Ltd., Maidstone, England).

Thereafter, 0.5 ml of the filtered supernatant was mixed with 2 ml of a solution of 0.05 M ONPG (Ortho-nitrophenol-β-D-galactopyranoside, Sigma Chemical Co., St. Louis, Mo. USA) preheated at 37° C. for 15 min, followed by incubation for 20 min at 37° C. After 20 min, the reaction was terminated with adding 0.5 ml of a 0.5 M Na$_2$CO$_3$ solution (Shinoyo Pure Chemical Co., Ltd., Osaka, Japan) thereto.

Absorbance at 420 nm was measured using a spectrophotometer (Beckman Du 650 spectrophotometer; Beckman Instrument, Inc, Fullerton, Calif., USA), and the results are given in FIG. 2.

Figure 2:
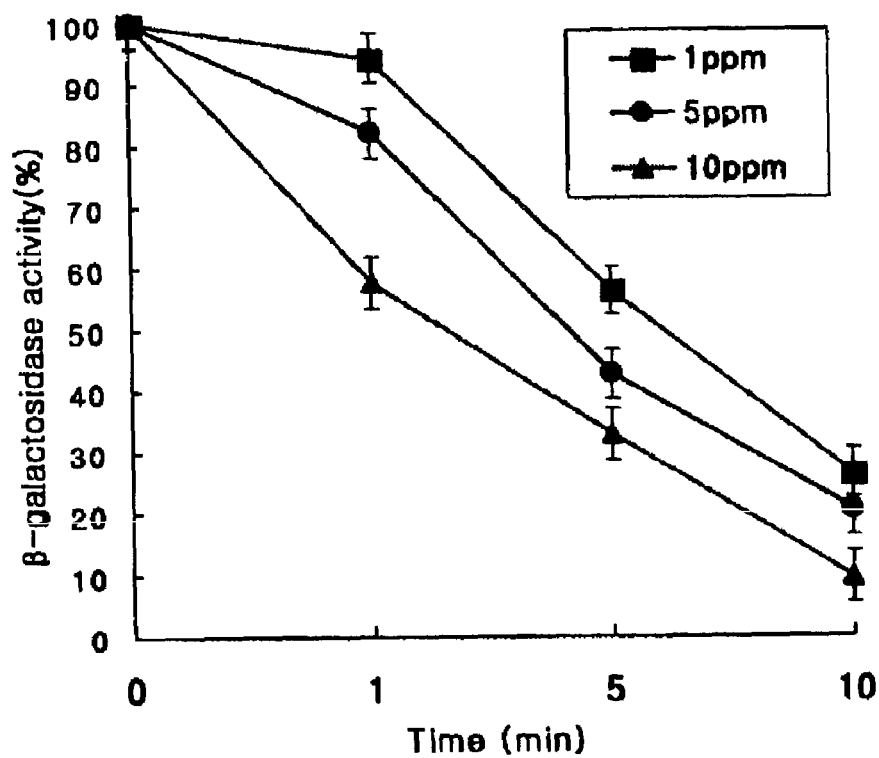
FIG. 2 is a graph showing an effect of ozone treatment on the activity of uncapsulated lactase.

As shown in FIG. 2, where the initial activity of lactase is 100%, when dispersion fluid of microcapsules was treated with 1 ppm of ozone for 1 min, it was found that the activity of lactase was reduced to about 94.3%. When being treated for 5 and 10 min, the activity of lactase was reduced to 56.4% and 26.5%, respectively.

When dispersion fluid was treated with 5 ppm of ozone for 1 min, the activity of lactase was reduced to 82%, and upon being treated for 5 and 10 min, the activity was reduced to 42.8% and 20%, respectively.

Sharply reduced lactase activities of 57.8%, 32.8% and 9.7% were observed with treatment of 10 ppm of ozone for 1, 5 and 10 min, respectively.

Experimental Example 2

Effect of Ozone Treatment on the Activity of Microencapsulated Lactase

With an aim to investigate effect of ozone treatment on microencapsulated lactase, microcapsules containing lactase were collected from the ozone-treated dispersion fluid prepared in Examples 2 to 4 by centrifugation, and the activity of microencapsulated lactase was measured using a heating method among yield analysis methods disclosed in Korean Pat. No. 88465.

0.5 ml of the resulting dispersion fluid containing microcapsules was mixed with 2 ml of 0.05 M ONPG pre-heated at 50° C. for 10 min. After 5 min, the reaction was terminated with adding 0.5 ml of 0.5M Na$_2$CO$_3$ thereto, and absorbance at 420 nm was measured using a spectrophotometer (Beckman Du 650 spectrophotometer, Beckman Instrument, Inc., Fullerton, Calif., USA). The results are given in FIG. 3, where the initial activity of lactase is 100%.

Figure 3:
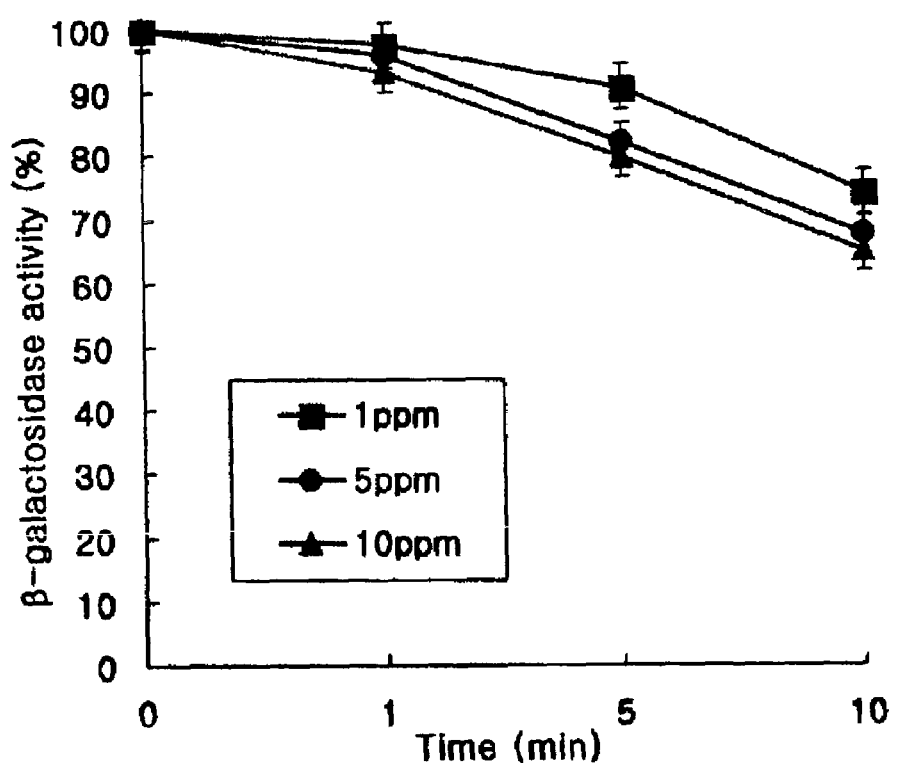
FIG. 3 is a graph showing an effect of ozone treatment on the activity of microencapsulated lactase.

As apparent in FIG. 3, the activity of lactase entrapped into microcapsules was reduced with increasing ozone concentration and treatment time of ozone. That is, when dispersion fluid of microcapsules was treated with 1 ppm of ozone for 1 min, it was found that the activity of lactase was reduced to about 97%. When being treated for 5 and 10 min, the activity of lactase was reduced to 91% and 74%, respectively.

Also, the activity of lactase was reduced to 96%, 82%, and 67% with the treatment of 5 ppm of ozone for 1, 5, and 10 min, respectively, and reduced lactase activities of 93%, 79% and 65% were observed with treatment of 10 ppm of ozone for 1, 5 and 10 min, respectively.

Collectively, similar activity, which was slightly reduced in comparison with initial activity, was observed in microencapsulated lactase treated with 1 ppm and 5 ppm for 1 min, and also, when microcapsules were treated with ozone of 5 ppm and 10 ppm, lactase activities were reduced in a similar pattern with increased treatment time of ozone.

These results demonstrate that ozone treatment reduces the activity of microencapsulated lactase, thus reducing yield of microcapsule to about 51%, while yield of microcapsules not treated with ozone was 78%, where the yield of microcapsules was calculated according to the following formula:

Yield of microcapsule=1−Activity of uncapsulated lactase/Initial activity of lactase×100

Such a reduced activity of microencapsulated lactase enzymes can be partially induced by other factors, such as pressure produced during a microencapsulation process or heat required to measure the yield of microcapsules, but it is believed that the ozone treatment is a major cause of the reduced yield.

Experimental Example 3

Effect of Ozone Treatment on Growth of Microorganisms

Microorganisms were treated with ozone of 10 ppm, at which concentration much of untrapped lactase loses its activity, while microencapsulated lactase retains effective activity, and effect of ozone on the growth of microorganisms was investigated.

Pathogenic microorganisms found especially in food, including *Escherichia coli, Bacillus subtilis, Staphylococcus aureus, Salmonella typhimurium, Pseudomonas aeruginosa,* and *Enterobacter aerogenes,* were obtained from Korean Culture Center of Microorganisms (Seoul, Korea) and stored in broth containing 50% glycerol at $-70°$ C. until use. The five strains, except *S. aureus,* were cultured in nutrient broth (NB), and *S. aureus* was cultured in tryptic soy broth (TSB) for 24 hours at $37°$ C.

Trace amounts of the cultured microorganisms were mixed with the dispersion fluid of microcapsules, followed by treatment of ozone of 10 ppm at $2°$ C. under a flow rate of 10 L/min using an ozone generator.

After being serially diluted, the ozone-treated microorganisms were plated onto nutrient agar broth. After incubation of 24–72 hours at optimum temperature, formed colonies were counted, and the results are given in Table 1, below.

TABLE 1

Control effect of ozone treatment on microorganism growth ( CFU/ml, % )

| Strain | Treatment time of ozone (min) | | | | |
|---|---|---|---|---|---|
| | 0 | 0.5 | 1 | 5 | 10 |
| *Escherichia coli* | $2.4 \times 10^9$ (100) | $8.9 \times 10^7$ (3.7) | $3.1 \times 10^7$ (1.3) | $9.0 \times 10^6$ (0.3) | 0 (0) |
| *Bacillus subtilis* | $1.6 \times 10^8$ (100) | $9.6 \times 10^7$ (60) | $2.2 \times 10^7$ (14) | $6.0 \times 10^6$ (3.7) | 0 (0) |
| *Staphylococcus aureus* | $6.8 \times 10^8$ (100) | $1.0 \times 10^8$ (15) | $6.4 \times 10^7$ (9.4) | $1.2 \times 10^7$ (1.8) | $1.1 \times 10^5$ (0.01) |
| *Salmonella typhimurium* | $2.5 \times 10^9$ (100) | $8.4 \times 10^8$ (34) | $1.1 \times 10^7$ (0.4) | $1.5 \times 10^6$ (0.06) | 0 (0) |
| *Pseudomonas aeruginosa* | $3.4 \times 10^8$ (100) | $1.2 \times 10^8$ (35) | $7.5 \times 10^7$ (22) | $3.6 \times 10^6$ (1.0) | 0 (0) |
| *Enterobacter aerogenes* | $1.4 \times 10^7$ (100) | $5.4 \times 10^6$ (38) | $1.0 \times 10^6$ (7.1) | $2.4 \times 10^5$ (1.7) | 0 (0) |

As shown in Table 1, it was found that five strains of microorganisms except *S. aureus* were killed when being exposed to ozone for 10 min. The highest sensitivity to ozone was observed in *E. coli,* showing viability of 3.7% even when being treated for 30 sec.

Also, viability of *S. typhimurium* dropped to 0.4% by ozone treatment for 1 min, while being 34% when treated for 30 sec. *P. aeruginosa* showed viability of 22% and 1% when treated for 1 and 5 min, respectively.

When the dispersion fluid containing *B. subtilis* and *E. aerogenes* was treated with ozone for 30 sec, viabilities were sharply reduced to 60% and 38%, respectively, whereas such a large reduction in viability was not observed upon ozone treatment for 1 and 5 min.

These results were correspondent to the fact that treatment with low concentration of ozone rarely affects the growth of microorganisms, whereas most of them are killed at a time at certain concentrations above threshold dose, which is disclosed by Broadwater, et al., (Broadwater et al., 1973, Sensitivity of three selected bacterial species to ozone, Applied Microbiology. 26(3):391–393). In addition, optimum treatment time and concentration of ozone varied according to the strains of microorganisms.

Experimental Example 4

Sensory Property of Milk Containing Microencapsulated Lactase During Storage Lactase-containing microcapsules, which were treated with 10 ppm of ozone for 10 min, were added into milk in an amount of 2% and 4%, and the milk was stored at $5°$ C. for 1, 3, 5, 8, and 12 days to evaluate sensory property of the milk. Sensory evaluation for sweetness of the milk was performed using Duncan's multiple range test.

Trained people having excellent ability to distinguish taste of milk evaluated the sweetness of the milk. The results are given in Table 2, below, where sensory property of the milk was scored on a five-point scale (1=none, 2=slight, 3=moderate, 4=sweet, and 5=very sweet). The data were obtained by analysis of variance (ANOVA) using a SAS program (1985), and differences among cases were determined through LSD (Least Significant Difference) test at $p<0.05$.

TABLE 2

Sweetness of milk containing microencapsulated lactase during storage

| Concentration of microcapsules (%) | Storage period (day) | | | | |
|---|---|---|---|---|---|
| | 1 | 3 | 5 | 8 | 12 |
| 0 | 1.0 | 1.0 | 1.0 | 1.0 | 1.0 |
| 2 | 1.0 | 1.0 | 1.0 | 1.12 | 1.38 |
| 4 | 1.0 | 1.0 | 1.38 | 1.63 | 1.75 |

As shown in Table 2, sweetness of milk was increased with longer period of storage, while scores of sweetness of milks were found to differ slightly according to concentration of added microcapsule.

In the milk containing 2% microcapsules, no significant difference in sweetness was observed during 5 days of storage, in comparison with the milk not containing lactase, and the sweetness was significantly ($p<0.05$) increased after days 8. Also, in the milk containing 4% microcapsules, no significant difference in sweetness was found by days 3 of storage, and the sweetness was significantly ($p<0.05$) increased from days 5.

On the whole, it was found that the milk containing lactase-containing microcapsules that were treated with ozone has preferable sensory property of sweetness during storage, resulting from that the disinfection action of ozone removing contaminants, especially microorganisms, which had been contained in the milk upon adding microcapsules, and thus ensuring better taste of the milk while maintaining freshness of the milk.

INDUSTRIAL APPLICABILITY

As described hereinbefore, an ozone treatment of dispersion fluid of microcapsules containing enzymes makes it possible to effectively remove uncapsulated enzymes as well as control the growth of microorganisms that may be harmful to human beings, resulting in preferable sensory property of sweetness of milk. Accordingly, the treatment of enzymes-entrapping microcapsules with ozone is very useful in enzyme-utilizing fields including the food industry, medical and pharmaceutical, and detergent industry.

The invention claimed is:

1. A method of removing residual enzymes when microencapsulating enzymes, comprising the step of treating dispersion fluid of microcapsules containing enzymes with an effective amount of ozone, thereby inactivating enzymes remaining in an uncapsulated form.

2. The method as set forth in claim 1, wherein the ozone is added in an amount of 1–10 ppm for 1–10 min.

3. The method as set forth in claim 1 or 2, wherein the ozone is generated by UV light from an ultraviolet lamp at a wavelength ranging from 150 to 200 nm.

4. The method as set forth in claim 1 or 2, wherein the ozone is added under a dry oxygen pressure of 0.4–0.6 kg/cm$^2$ and a flow rate of 5–15 L/min.

* * * * *